United States Patent
Kwok et al.

(10) Patent No.: US 7,630,763 B2
(45) Date of Patent: Dec. 8, 2009

(54) THORACIC OR INTRACARDIAC IMPEDANCE DETECTION WITH AUTOMATIC VECTOR SELECTION

(75) Inventors: Jonathan Kwok, Shoreview, MN (US); Kent Lee, Shoreview, MN (US); Jesse W. Hartley, Lino Lakes, MN (US); Jeffrey E. Stahmann, Ramsey, MN (US); Yinghong Yu, Shoreview, MN (US); Jiang Ding, Maplewood, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 762 days.

(21) Appl. No.: 11/110,418

(22) Filed: Apr. 20, 2005

(65) Prior Publication Data

US 2006/0241512 A1    Oct. 26, 2006

(51) Int. Cl.
*A61B 5/053* (2006.01)
*A61B 5/0295* (2006.01)

(52) U.S. Cl. ............................. 607/6; 607/27; 607/28

(58) Field of Classification Search ............... 600/513, 600/526, 627, 529, 547, 485, 484; 607/20, 607/122
See application file for complete search history.

(56) References Cited

U.S. PATENT DOCUMENTS

| | | | | |
|---|---|---|---|---|
| 4,757,824 A | * | 7/1988 | Chaumet | 600/529 |
| 4,870,578 A | * | 9/1989 | Vysin et al. | 600/509 |
| 5,178,151 A | * | 1/1993 | Sackner | 600/485 |
| 5,318,597 A | | 6/1994 | Hauck et al. | |
| 5,735,286 A | * | 4/1998 | Notton et al. | 600/513 |
| 5,824,029 A | * | 10/1998 | Weijand et al. | 607/122 |
| 6,076,015 A | * | 6/2000 | Hartley et al. | 607/20 |
| 6,104,949 A | * | 8/2000 | Pitts Crick et al. | 600/547 |
| 6,266,554 B1 | | 7/2001 | Hsu et al. | |
| 6,292,689 B1 | * | 9/2001 | Wallace et al. | 600/547 |

(Continued)

FOREIGN PATENT DOCUMENTS

EP        0310024 A2    4/1989

(Continued)

OTHER PUBLICATIONS

"International Search Report and Written Opinion for Application No. PCT/US2006/009646, date mailed Jul. 25, 2006", 12 Pages.

(Continued)

*Primary Examiner*—Carl H Layno
*Assistant Examiner*—Luther G Behringer
(74) *Attorney, Agent, or Firm*—Schwegman, Lundberg Woessner, P.A.

(57) ABSTRACT

This document discusses, among other things, a cardiac function management device or other implantable medical device that includes a test mode and a diagnostic mode. During a test mode, the device cycles through various electrode configurations for collecting thoracic impedance data. At least one figure of merit is calculated from the impedance data for each such electrode configuration. In one example, only non-arrhythmic beats are used for computing the figure of merit. A particular electrode configuration is automatically selected using the figure of merit. During a diagnostic mode, the device collects impedance data using the selected electrode configuration. In one example, the figure of merit includes a ratio of a cardiac stroke amplitude and a respiration amplitude. Other examples of the figure of merit are also described.

27 Claims, 8 Drawing Sheets

U.S. PATENT DOCUMENTS

| | | |
|---|---|---|
| 6,308,095 B1 | 10/2001 | Hsu et al. |
| 6,438,410 B2 | 8/2002 | Hsu et al. |
| 6,449,503 B1 | 9/2002 | Hsu |
| 6,449,509 B1 * | 9/2002 | Park et al. .................... 607/20 |
| 6,602,201 B1 * | 8/2003 | Hepp et al. ................. 600/526 |
| 7,160,252 B2 * | 1/2007 | Cho et al. ................... 600/484 |
| 2005/0065447 A1 * | 3/2005 | Lee et al. .................... 600/529 |
| 2005/0085734 A1 | 4/2005 | Tehrani |
| 2005/0182447 A1 | 8/2005 | Schecter |

FOREIGN PATENT DOCUMENTS

| | | |
|---|---|---|
| EP | 0510456 A1 | 10/1992 |
| EP | 0576114 A2 | 12/1993 |
| WO | WO 2006/115607 * | 2/2006 |
| WO | WO-2006115607 A1 | 11/2006 |

OTHER PUBLICATIONS

Zhang, Yunlong, "Intracardiac Impedance and Its Applications", U.S. Appl. No. 11/208,922, filed Aug. 22, 2005, 36 Pgs.

"European Application Serial No. 06738680.5, Office Action mailed Sep. 11, 2008", 2 pgs.

* cited by examiner

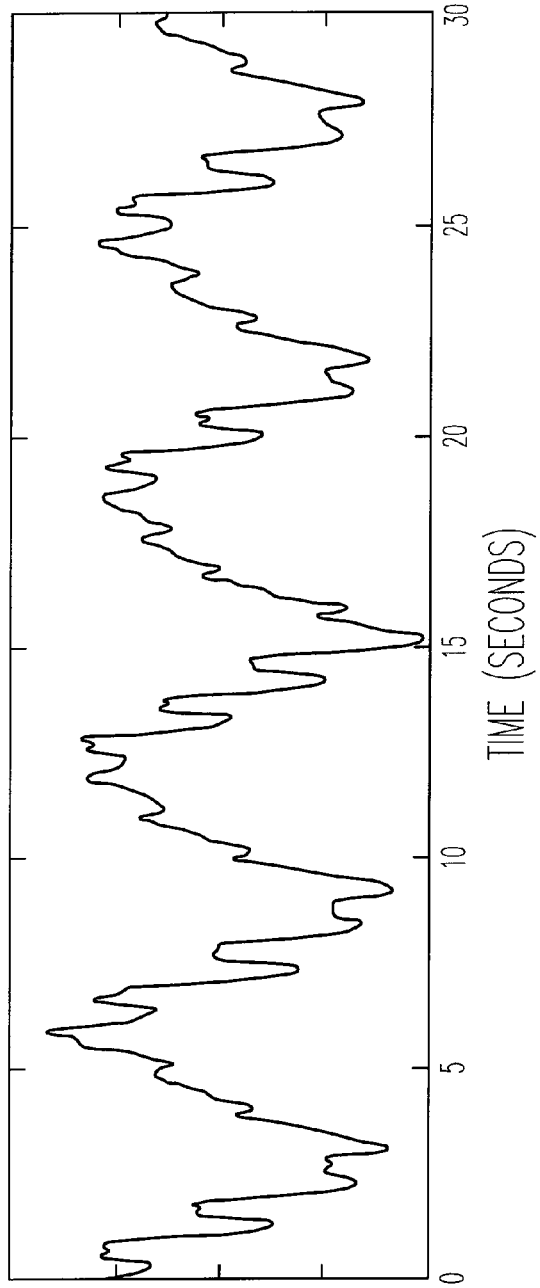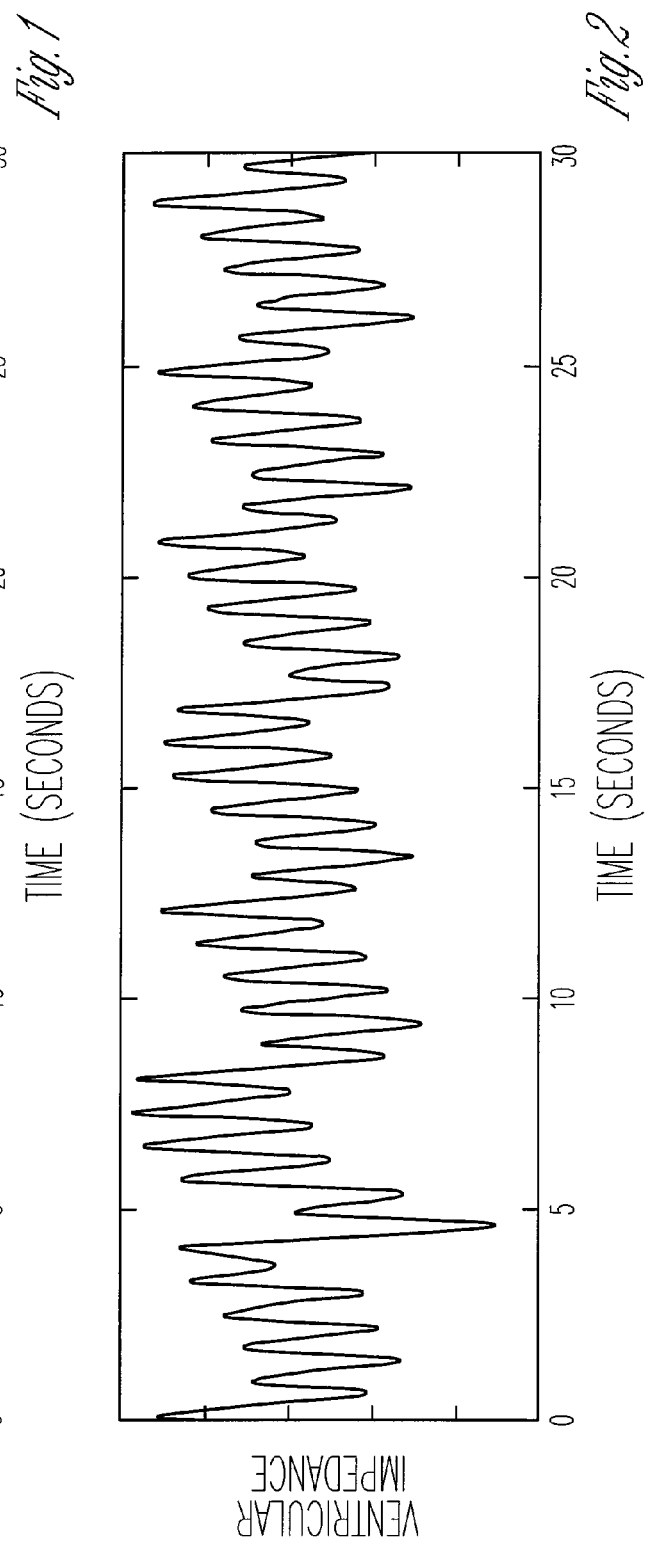

THORACIC OR INTRACARDIAC IMPEDANCE DETECTION WITH AUTOMATIC VECTOR SELECTION

TECHNICAL FIELD

This document pertains generally to implantable medical devices and more particularly, but not by way of limitation, to thoracic or intracardiac impedance detection with automatic vector selection.

BACKGROUND

Implantable medical devices include, among other things, cardiac function management (CFM) devices such as pacers, cardioverters, defibrillators, cardiac resynchronization therapy (CRT) devices, as well as combination devices that provide more than one of these therapy modalities to a subject. Such devices often include one or more diagnostic capabilities. Moreover, such diagnostic capabilities may be used as a basis for automatically providing therapy to the subject or for communicating diagnostic information to a physician or to the subject.

One example of a diagnostic capability is sensing intrinsic electrical heart signals. These intrinsic heart signals include depolarizations that propagate through heart tissue. The depolarizations cause heart contractions for pumping blood through the circulatory system. The intrinsic heart signals are typically sensed by an implantable medical device at implanted electrodes. The implantable medical device typically includes sense amplifier circuits and other signal processing circuits to extract useful diagnostic information from the intrinsic heart signals.

A different example of a diagnostic capability is sensing an interelectrode impedance, that is, detecting an impedance between electrodes. Such electrodes typically include, among other things, electrodes that are implanted in a subject's thorax. Electrodes that are implanted in a subject's thorax may include, among other things, "intracardiac" electrodes located within the subject's heart. Another example of thoracic electrodes includes intravascular electrodes located in the subject's vasculature. A further example of thoracic electrodes includes epicardial electrodes that are located on an outer surface of the subject's heart. Yet another example of thoracic electrodes includes housing electrodes that are located on a typically hermetically sealed "can" of a pectorally or abdominally implanted CRM device electronics unit, or on an insulating "header" of such an electronics unit.

A tissue impedance between electrodes is typically obtained by introducing a test current into the tissue and sensing a responsive voltage between two electrodes (or vice-versa). The electrodes used for introducing a test current or test voltage need not be the same electrodes as those used for respectively measuring the responsive voltage or responsive current.

An impedance signal obtained between two intracardiac electrodes will be affected and modulated by, among other things, the subject's heart contractions and the subject's breathing. These two impedance-derived signals are sometimes referred to as the cardiac stroke signal and the respiration signal, respectively. Each provides useful diagnostic information. For example, the cardiac stroke signal may be used as an input variable to responsively adjust a pacing rate or another parameter of a "stroke volume" or other cardiac pacing therapy algorithm. Similarly, the respiration signal (e.g., amplitude, frequency, etc.) may be used as an input variable to responsively adjust a pacing rate or another parameter of a "minute ventilation" or other cardiac pacing therapy algorithm. In sum, the impedance-derived cardiac stroke and respiration signals can provide useful diagnostic information for a cardiac rhythm management device.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

FIG. 1 illustrates one example of thoracic impedance data obtained using an atrial lead electrode.

FIG. 2 illustrates one example of thoracic impedance data obtained using a ventricular lead electrode.

DETAILED DESCRIPTION

Figure 3:
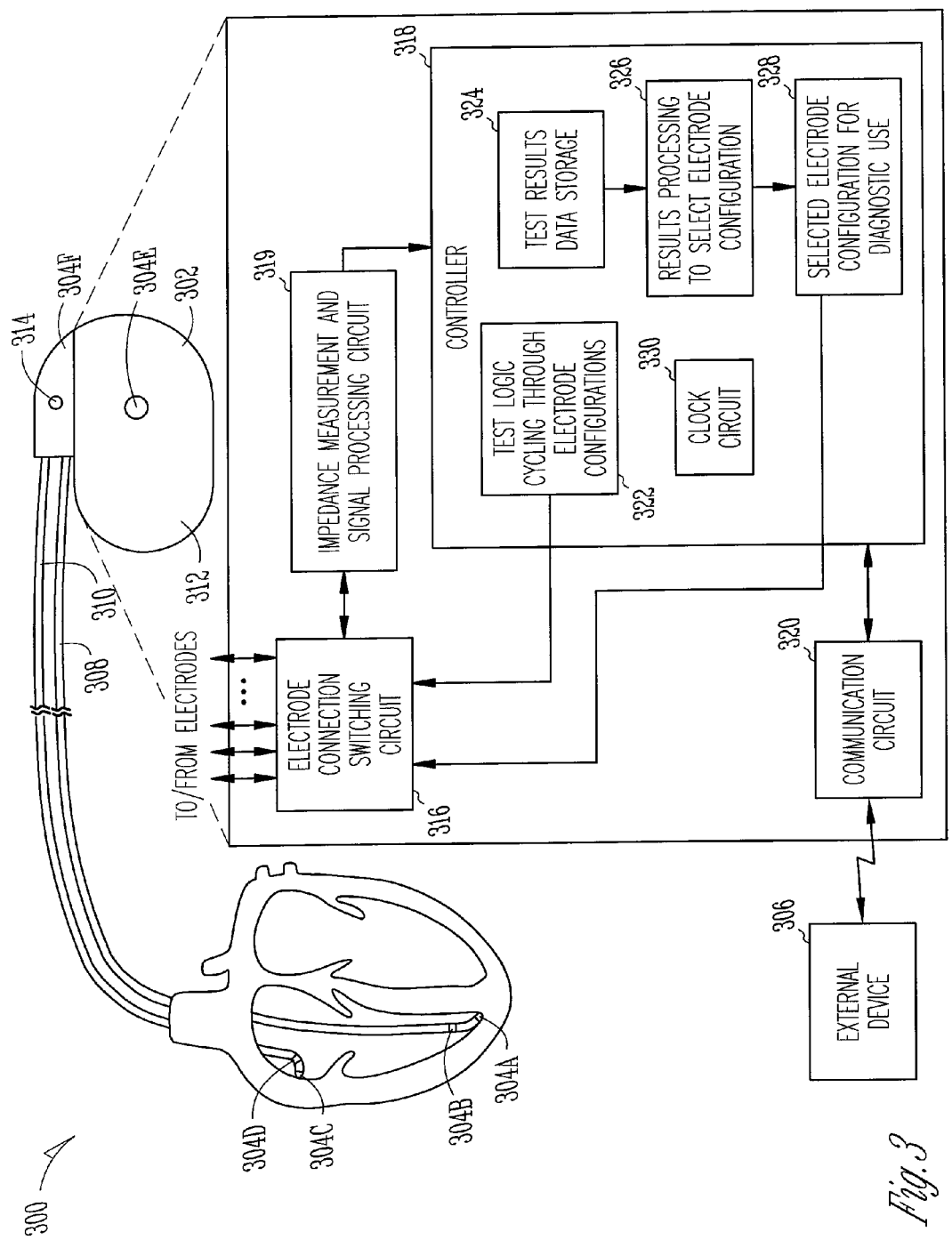
FIG. 3 is a block diagram illustrating generally one example of a system and environment for measuring an intracardiac or transthoracic impedance in a diagnostic mode, and including a test mode for determining which electrode configuration to automatically select for use for collecting the impedance data in the diagnostic mode.

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

Overview of Research Study

A rate responsive pacer may use an impedance sensor to measure trans-thoracic impedance. In one example, such thoracic impedance is measured between an intracardiac electrode on the pacer lead ("lead electrode") and another electrode on a pectorally-located pacer "can" housing electronics and a power source. This measured thoracic impedance includes, among other things, both a respiratory component and cardiac contraction volume ("cardiac stroke") component. At least some of the present inventors participated in conducting a research study that compared the thoracic impedance signal between different lead electrode locations (ventricular vs. atrial), and pacer can implant sites (left pectoral implant vs. right pectoral implant).

In this research study, thoracic impedance sensor signals were recorded from 30 patients with PULSAR MAX I/II or INSIGNIA+ pacer devices from Guidant Corp. These patients were divided into four groups. The first group (designated the "AR" group) had thoracic impedance measured between (1) a lead electrode associated with a right atrium and (2) a right pectoral can electrode. The second group (designated the "AL" group) had thoracic impedance measured between (1) a lead electrode associated with a right atrium and (2) a left pectoral can electrode. The third group (designated the "VR" group) had thoracic impedance measured between (1) a lead electrode associated with a right ventricle and (2) a right pectoral can electrode. The fourth group (designated the "VL" group) had thoracic impedance measured between (1) a lead electrode associated with a right ventricle and (2) a left pectoral can electrode.

For each of these four groups of patients, the thoracic impedance signal was analyzed during a 30 second window of regular respiration while the patient was supine. The peak-to-peak respiration and cardiac contraction volume ("stroke") components of the thoracic impedance signal were extracted and averaged. The respiration/stroke amplitude ratio values were compared between the four groups of patients. Statistical significance was determined with an unpaired two-tailed t-test. The results are presented below as a mean±standard deviation.

Atrial lead electrode thoracic impedance signals (from the AR and AL groups) typically exhibited a larger respiration/stroke amplitude ratio than ventricular-electrode thoracic impedance signals (from the VR and VL groups). The respiration/stroke amplitude ratio among AR patients (n=10) was 1.68±0.93, among AL patients (n=2) was 0.80±0.23, among VR patients (n=3) was 0.71±0.69, and among VL patients (n=15) was 0.74±0.35.

The respiration/stroke amplitude ratio for atrial lead electrode thoracic impedance signals, regardless of whether the can is implanted near the right or left pectoral region, was 1.53±0.91. By contrast, the respiration/stroke amplitude for ventricular lead electrode thoracic impedance signals, regardless of whether the can is implanted near the right or left pectoral region, was 0.74±0.39. This difference was deemed highly significant (p<0.005). The respiration component of thoracic impedance was found to be larger in the AR patients than all of the other tested electrode configurations. These other electrode configurations were found to be dominated by the cardiac stroke signal instead of the respiration signal.

In general, the different respiration and stroke amplitudes of the thoracic impedance signal depends on lead electrode location (atrium versus ventricle) and pocket location where the can electrode is located (left versus right pectoral region). For example, FIG. 1 illustrates one example of thoracic impedance data obtained from a first patient using an atrial lead electrode. FIG. 2 illustrates one example of thoracic impedance data obtained from a second patient using a ventricular lead electrode. Comparing FIG. 1 to FIG. 2, it is seen that the atrial lead electrode of FIG. 1 yielded a stronger respiration component of thoracic impedance.

Therefore, different electrode positions exhibit different combinations of cardiac stroke information and respiration information. This observation can be used to select the electrode configuration that has the best signal-to-noise ratio (SNR) for the information component (e.g. cardiac stroke or respiration) that is desired.

Examples of Systems and Methods

FIG. 3 is a block diagram illustrating generally one example of a system 300 and environment for measuring an intracardiac or transthoracic impedance in a diagnostic mode, and including a test mode for determining which electrode configuration to automatically select for use in subsequently collecting the impedance data in the diagnostic mode. In this example, the system 300 includes a cardiac function management (CFM) or other implantable medical device (IMD) 302, electrodes 304 to collect impedance data, and an external device 306 to communicate with the IMD 302.

In the example of FIG. 3, the electrodes 304 include a distal tip electrode 304A and slightly more proximal ring electrode 304B, each located on a portion of a right ventricular intravascular lead 308. This example also includes a distal tip electrode 304C and a slightly more proximal ring electrode 304D, each located on a portion of a right atrial intravascular lead 310. This example further includes a "can" or "housing" electrode 304E located on an external housing 312 of an electronics unit portion of the IMD 302. A "header" electrode 304F is located on an insulating header 314 of the electronics unit portion of the IMD 302, wherein the header 314 typically extends outward from the housing 312. As explained below, the system 300 need not include or use all of these electrodes 304. The system 300 may also include additional or different electrodes such as, for example, defibrillation electrodes. Moreover, the illustrated electrodes may additionally be used for other purposes, such as for sensing intrinsic electric heart signals or for providing pacing therapy. FIG. 3 merely provides one illustrative example of electrodes for making impedance measurements.

FIG. 3 also illustrates one example of a block diagram of certain components included within the housing 312 of the IMD 302. In this example, such components include an electrode connection switching circuit 316. The electrode connection switching circuit 316 makes appropriate electrical connections to various combinations of the electrodes 304, such as in response to one or more selection control signals received from a controller circuit 318. These electrical connections to the desired electrodes 304 are routed to an impedance measurement and signal processing circuit ("impedance circuit") 319. Examples of some electrode configurations and suitable circuits for performing thoracic impedance measurements and further signal processing are described in Hartley et al. U.S. Pat. No. 6,076,015 entitled RATE ADAPTIVE CARDIAC RHYTHM MANAGEMENT DEVICE USING TRANSTHORACIC IMPEDANCE and Hauck et al. U.S. Pat. No. 5,318,597 entitled RATE ADAPTIVE CARDIAC RHYTHM MANAGEMENT DEVICE CONTROL ALGORITHM USING TRANS-THORACIC VENTILATION, each of which are assigned to Cardiac Pacemakers, Inc., and each of which is incorporated herein by reference in its entirety, including their description of electrode configurations, impedance measurements, and further signal processing of impedance signals. The impedance circuit 319 provides resulting impedance information to the controller 318 for further processing.

The controller 318 is typically a microprocessor or any other circuit that is capable of sequencing through various control states such as, for example, by using a digital microprocessor having executable instructions stored in an associated instruction memory circuit, a microsequencer, or a state machine. In one example, the controller 318 includes a digital signal processor (DSP) circuit. The digital signal processor circuit may performs digital filtering or other signal processing of the impedance signal, either instead of, or in addition to such processing being performed in the impedance circuit 319. The digital signal processor circuit, therefore, may implement one or more filter circuits, and such filter circuits may be implemented as a sequence of executable instructions, rather than by dedicated filtering hardware.

The controller 318 typically includes a diagnostic mode in which the received impedance information is used as diagnostic information. In one example, the impedance-based diagnostic information is wirelessly or otherwise communicated, via a communication circuit 320, from the IMD 302 to an external device 306, such as for use by a remote or local physician or other caregiver. In another example, the impedance-based diagnostic information is used by pacing or other therapy algorithm, such as to establish an appropriate pacing rate, atrioventricular (AV) or other interelectrode delay, or other adjustable therapy parameter.

In one example, the controller 318 also includes a test mode. The test mode activates algorithmic or other test logic 322 that cycles through various electrode configurations. Such cycling allows the impedance circuit 319 to obtain an impedance signal from each such electrode configuration. The resulting test mode impedance data, corresponding to each of the tested electrode configurations, is stored in a test results data storage circuit 324, such as in a memory circuit portion of the controller 318 or elsewhere. The controller 318 typically includes a results processing algorithm 326 to select a particular electrode configuration by analyzing the impedance data resulting from the various tested electrode configurations. Information defining the particular selected electrode configuration is stored in a memory location 328. In one example, after the test mode data is collected and the particular electrode configuration is selected, the device 302 exits the test mode and enters a diagnostic mode. The electrode configuration that was selected during the test mode is used in the diagnostic mode to obtain impedance data for diagnostic purposes. In one example, the test mode is initiated by the external device 306, for example, either automatically or under manual control of a physician or other caregiver. In another example, the test mode is internally initiated automatically by the IMD 302, such as by being occasionally or periodically triggered by an interrupt provided by a clock circuit 330 of the controller 318 or elsewhere within the IMD 302. In yet another example, the test mode is internally initiated automatically by the IMD 302, such as by being automatically triggered by a change in posture or heart rate respectively detected by a posture detector or heart rate detector included within the IMD 302 and coupled to an input of the test logic 322.

The illustrative example of FIG. 3 includes multiple electrode configurations from which impedance data can be obtained. For example, a first electrode configuration includes delivering a test current from the right atrial tip electrode 304C to the housing electrode 304E and determining an impedance by measuring a resulting voltage between the right atrial ring electrode 304D and the header electrode 304F. A second electrode configuration includes delivering the test current from the right ventricular tip electrode 304A to the housing electrode 304E and determining an impedance by measuring a resulting voltage between the right ventricular ring electrode 304B and the header electrode 304F. These are merely illustrative examples of different electrode configurations for performing impedance measurements. Other examples exist. Moreover, such impedance measurements need not require the use of four different electrodes, as described above, but can also use two electrodes, three electrodes, or more than four electrodes. Furthermore, one or more of the electrodes may be electrically connected in common with one or more other electrodes for performing the impedance measurements.

Figure 4:
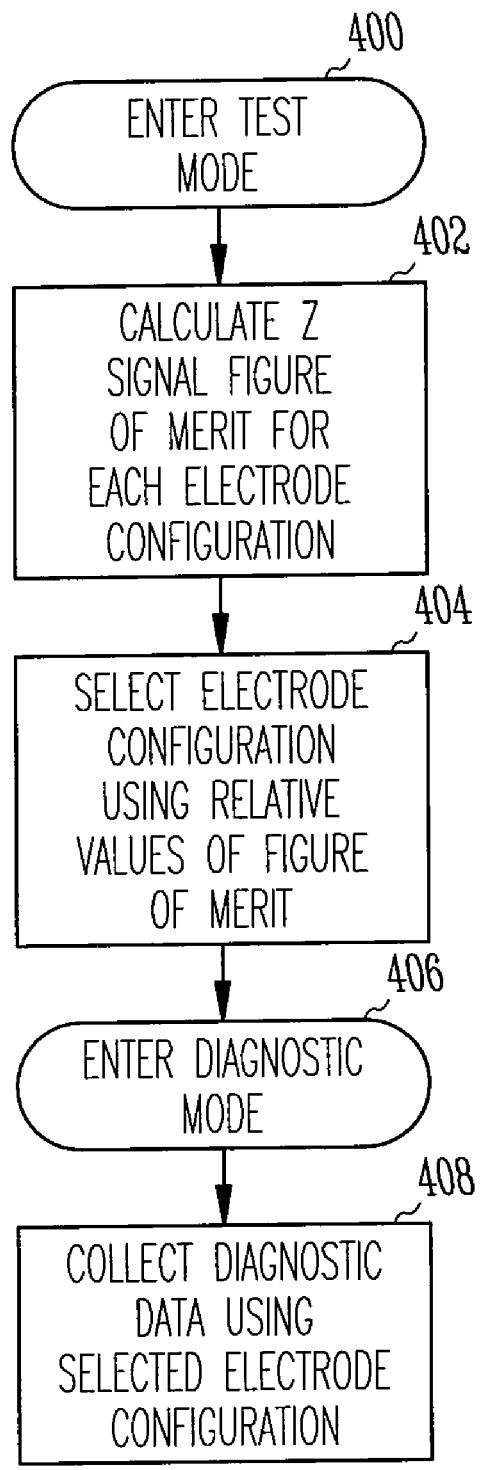
FIG. 4 is a flow chart of one example of a method of using the system of FIG. 3 or a similar system.

FIG. 4 is a flow chart of one example of a method of using the system 300 of FIG. 3 or a similar system. In this example, at 400, a test mode is entered, such as upon manual initiation by a physician or other caregiver using the external device 306, or automatically, such as upon a scheduled interrupt received from the clock circuit 320 or otherwise. At 402, an impedance signal figure of merit is calculated for each electrode configuration, for example, in a predefined list of available electrode configurations for measuring an impedance. This typically constitutes using each such available electrode configuration to measure an impedance signal, perform signal processing on the impedance signal to extract a desired component of the impedance signal (e.g., the respiration modulation component, the cardiac stroke signal modulation component, the ultra low frequency edema/hypotension component, postural component, etc.), and measuring a desired characteristic (e.g., modulation amplitude), undesired characteristic (e.g., noise), or combination characteristic (e.g., signal-to-noise ratio). In this context, the noise can be from one or several sources, including myopotential noise, electromagnetic interference, or even from one or more of the undesired frequency components of the impedance signal. For example, if respiration is the desired component of the impedance signal, then, in one example, modulation of the impedance signal due to heart contractions (i.e., the cardiac stroke signal) is regarded as noise. Similarly, modulation of a thoracic impedance signal due to thoracic fluid shifts (e.g., edema, hypotension, postural changes, blood resistivity changes, etc.) are, in one example, regarded as noise when the desired component of the impedance signal is the respiration or cardiac stroke component. If the cardiac stroke signal is the desired component of the impedance signal, then, in one example, modulation of the impedance signal due to respiration is regarded as noise. In one example, the figure of merit is computed based upon a single measurement. In another example, the figure of merit is averaged from multiple measurements, or a central tendency of the figure of merit is otherwise computed and used as the figure of merit.

At 404, relative values of the figure of merit are compared to each other to select the most suitable electrode configuration for subsequent diagnostic data collection. For example, if respiration is the desired data of interest from the impedance signal, then the electrode configuration having the largest respiration signal amplitude (or variability or dynamic range of the respiration signal amplitude), the smallest noise, or the largest signal-to-noise ratio is selected. In one example, more than one of these figures of merit are collected, optionally weighted, and combined to form a composite figure of merit; the relative values of the composite figure of merit (or a computed central tendency of the composite figure of merit) are compared to select the most appropriate electrode configuration. In one example, the selection process includes at least one technique for breaking a "tie" resulting from equivalent relative values of the determinative figure(s) of merit. In one example, in which the available electrode configurations are listed in an ordered list, a tie between two or more electrode configurations yielding the same values of the determinative figure of merit is broken by selecting from among these tied candidate electrode configurations by selecting the electrode configuration that is closest to the beginning of the list.

After an electrode configuration is selected at 404, then, at 406, the test mode is exited and a diagnostic mode is entered. At 408, diagnostic data is collected using the selected electrode configuration. As discussed above, such diagnostic data can be used as an input variable for adjusting a cardiac rhythm management or other therapy, or can simply be communicated from the IMD 302, such as to a physician or other caregiver.

Figure 5:
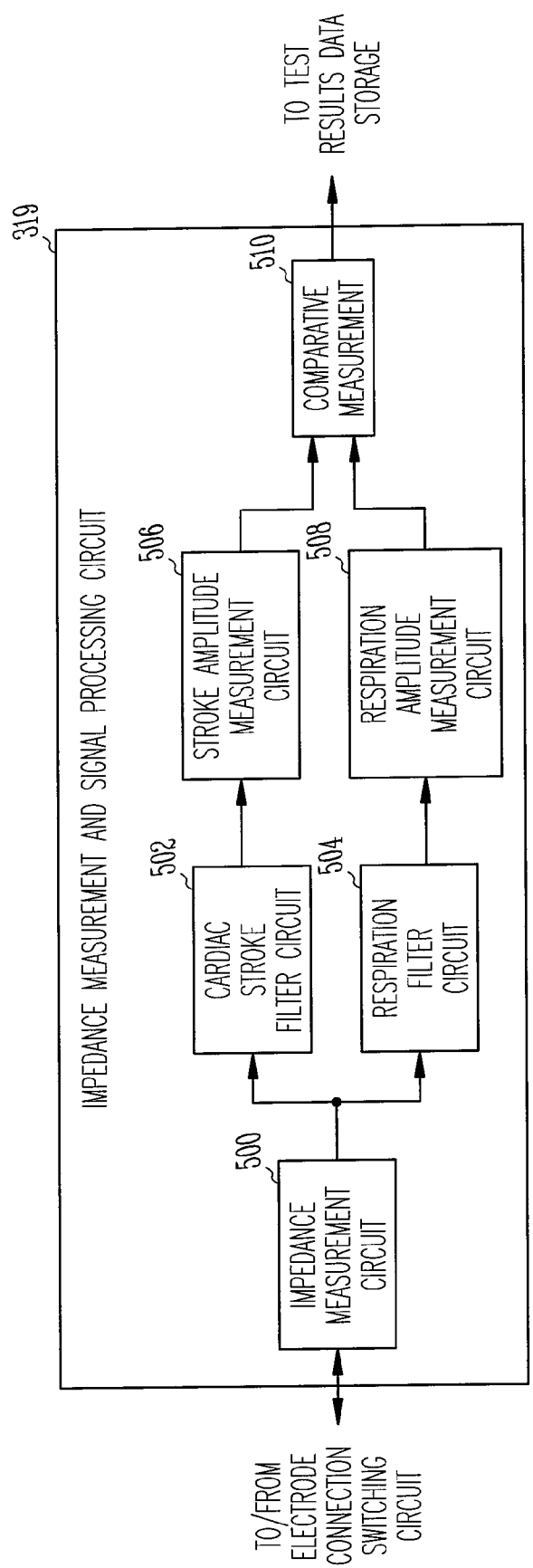
FIG. 5 is a block diagram of one illustrative example of more detail of portions of an impedance circuit.

FIG. 5 is a block diagram of one illustrative example of more detail of portions of the impedance circuit 319. In this example, the impedance circuit 319 includes an impedance measurement circuit 500, which is coupled to various configurations of the electrodes 304 via the electrode connection switching circuit 316. The impedance measurement circuit 500 typically includes an exciter circuit that provides a test current to the tissue between two electrodes in the heart or elsewhere in the thorax. The impedance measurement circuit 500 also typically includes preamplifier, demodulation, bandpass filter, and analog-to-digital converter circuits that are used to measures a responsive voltage between the same or different two electrodes to determine the impedance. Examples of such suitable subcircuits of the impedance measurement circuit 500 are described in Hartley et al. U.S. Pat. No. 6,076,015 entitled RATE ADAPTIVE CARDIAC RHYTHM MANAGEMENT DEVICE USING TRANSTHORACIC IMPEDANCE, which is assigned to Cardiac Pacemakers, Inc., and which is incorporated herein by reference in its entirety, including its description of such subcircuits and their operation.

In the example of FIG. 5, the impedance circuit 319 also includes a cardiac stroke filter circuit 502 and a respiration filter circuit 504 for respectively extracting a cardiac stroke component and a respiration component of the impedance signal. Such filter circuits can be implemented in dedicated analog or digital hardware, or as a sequence of instructions carried out on a general purpose digital signal processing circuit or more generic processor of the controller 318, such as described in the above-incorporated Hartley et al. U.S. Pat. No. 6,076,015. Moreover, such filtering may use a heart rate dependent or other variable cutoff frequency filter, such as described in the above-incorporated Hartley et al. U.S. Pat. No. 6,076,015. In this example, the impedance circuit 319 also includes a cardiac stroke amplitude measurement circuit 506 and a respiration amplitude measurement circuit 508 for respectively measuring amplitudes of the extracted cardiac stroke and respiration amplitude signals. In this illustrative example, these measured amplitudes are then fed to a comparative measurement circuit 510. In one example, the comparative measurement circuit 510 calculates at least one indication of the relative values of the cardiac stroke and respiration amplitudes, such as a respiration/stroke amplitude ratio, a stroke/respiration amplitude ratio, a respiration—stroke amplitude difference, or a stroke—respiration amplitude difference. In one example, the calculated indication of the relative values of the cardiac stroke and respiration amplitudes is stored in the test results data storage 324, and used as the electrode configuration figure of merit in the process described with respect to FIG. 4. For example, if respiration is the desired diagnostic component of the impedance, and the comparative measurement is a respiration/stroke ratio, then the electrode configuration having the largest relative value of respiration/stroke ratio is selected during the test mode for subsequent data collection in the diagnostic mode.

Figure 6:
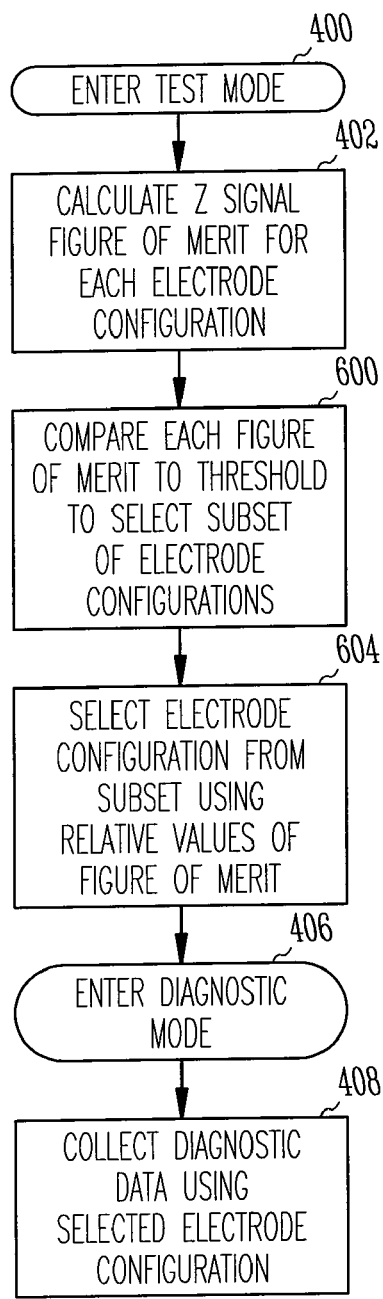
FIG. 6 is a flow chart of another example of a process that is similar to that of FIG. 4.

FIG. 6 is a flow chart of another example of a process that is similar to that of FIG. 4. In the example of FIG. 6, at 400, a test mode is entered and, at 402, at least one impedance signal figure of merit is calculated for each electrode configuration, as discussed above. However, the process of FIG. 6 then includes a screening, at 600, that compares at least one impedance signal figure of merit to a threshold value to select a subset of electrode configurations from which a particular electrode configuration is then selected, at 604, using relative values of the same or different figure of merit. The screening at 600 may, for example, compare a respiration amplitude to a minimum threshold value, such that only those electrode configurations yielding a minimum respiration amplitude become part of the subset of electrode configurations from which the particular electrode configuration is then selected at 604. As another example, the screening at 600 may compare noise figure of the respiration component of the impedance signal to a threshold value, such that only those electrode configurations yielding a sufficiently noise-free respiration component of the impedance signal become part of the subset of electrode configurations from which the particular electrode configuration is then selected at 604. The subset may be empty, in which case, the particular impedance-based diagnostic function is disabled, in one example. The subset may alternatively yield some or even all of the available electrode configurations. In the process illustrated in FIG. 6, after the particular electrode configuration is selected at 604, then the test mode is exited. The diagnostic mode is then entered, at 406. Diagnostic data is then collected at 408 using the selected electrode configuration.

Figure 7:
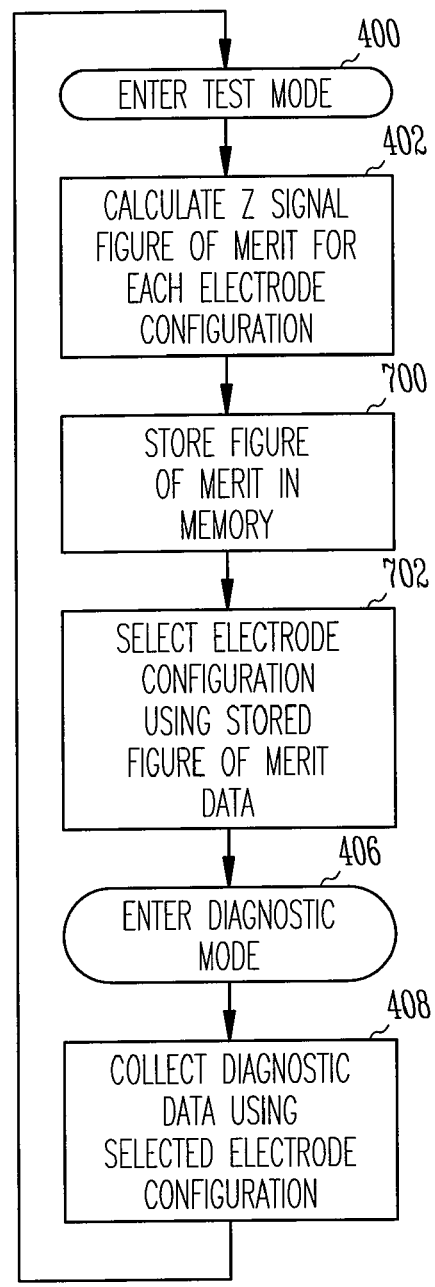
FIG. 7 is a flow chart of another example of a process that is similar to that of FIG. 4.

FIG. 7 is a flow chart of another example of a process that is similar to that of FIG. 4. In the example of FIG. 7, at 400, a test mode is entered and, at 402, at least one impedance signal figure of merit is calculated for each electrode configuration, as discussed above. However, the process of FIG. 7 then includes, at 700, storing the figure(s) of merit in memory, together with any previously stored historical values of the figure(s) of merit. In one example, such storage of each particular figure of merit occurs in a buffer that, when full, drops the oldest historical value of that figure of merit from the buffer. For example, if the amplitude of the respiration component of the impedance signal is used as the figure of merit, then the buffer would include its most recent value and other previously acquired values over an appropriate period of time. At 702, an electrode configuration is selected using the stored figure of merit data. As an illustrative example, suppose that respiration is of interest, and the dynamic range or variation of the respiration amplitude is of particular interest. Then in one example, a secondary figure of merit (e.g., variance, standard deviation, etc.) of the respiration amplitude is computed from the stored historical values of the primary figure of merit (respiration amplitude). Relative values of the secondary figure of merit are used at 702 to select the particular electrode configuration used for collecting diagnostic data. Then, at 406, the test mode is exited and the diagnostic mode is entered. At 408, diagnostic data is collected for a period of time using the selected electrode configuration. Process flow then returns to 400 to re-enter the test mode to again collect and store the figure of merit data.

Examples of Particular Electrode Configurations

The above-described systems and methods can be used to select between any different present or future electrode configuration to obtain a desirable SNR for the information sought (e.g., cardiac stroke information or respiration information, exclusively).

Figure 8:
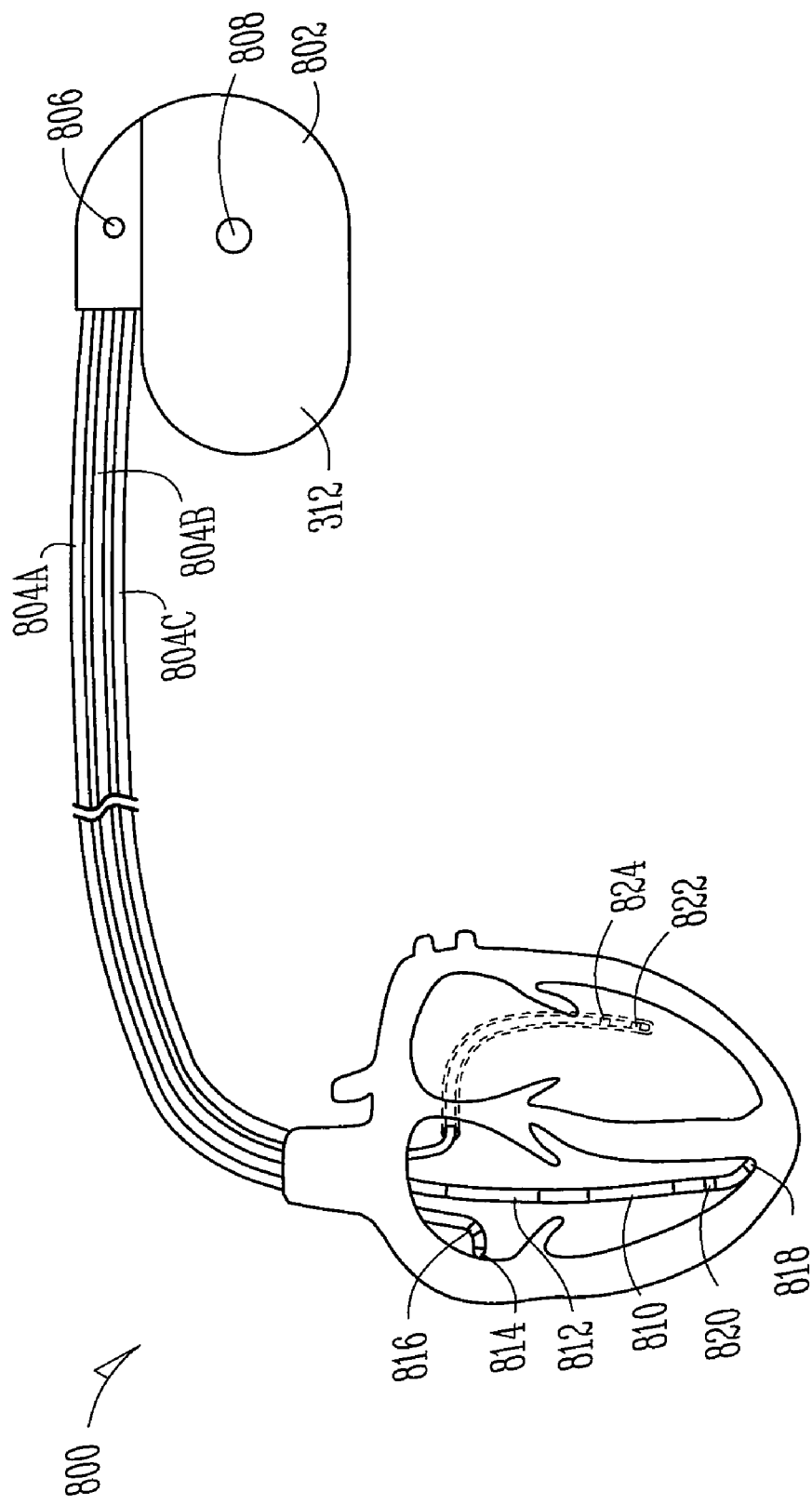
FIG. 8 is an example of a system that includes an implantable electronics unit, and leads extending into the right atrium, right ventricle, and coronary sinus, respectively.

As an illustrative example (but not by way of limitation), suppose the system 800 of FIG. 8 includes an implantable electronics unit 802, leads 804A-C (extending into the right atrium, right ventricle, and coronary sinus, respectively), and the available electrodes include: a header electrode such as 806, a can electrode such as 808, a right ventricular shock coil electrode 810, a right atrial shock coil electrode 812, a right atrial tip electrode 814, a right atrial ring electrode 816, a right ventricular tip electrode 818, a right ventricular ring electrode 820, a left ventricular distal electrode 822, and a left ventricular proximal electrode 824.

In this example, some of the possible voltage sensing or test excitation current vectors include, for pairs of electrodes: can electrode 808 to right ventricular shock coil electrode 810, can electrode 808 to right atrial shock coil electrode 812, can electrode 808 to right atrial tip electrode 814, can electrode 808 to right atrial ring electrode 816, can electrode 808 to right ventricular tip electrode 818, can electrode 808 to right ventricular ring electrode 820, can electrode 808 to left ventricular distal electrode 822, can electrode 808 to left ventricular proximal electrode 824, header electrode 806 to right ventricular shock coil electrode 810, header electrode 806 to right atrial shock coil electrode 812, header electrode 806 to right atrial tip electrode 814, header electrode 806 to right atrial ring electrode 816, header electrode 806 to right ventricular tip electrode 818, header electrode 806 to right ventricular ring electrode 820, header electrode 806 to left ventricular distal electrode 822, header electrode 806 to left ventricular proximal electrode 824, right ventricular shock coil electrode 810 to right atrial shock coil electrode 812, right ventricular shock coil electrode 810 to right atrial tip electrode 814, right ventricular shock coil electrode 810 to right atrial ring electrode 816, right ventricular shock coil electrode 810 to right ventricular tip electrode 818, right ventricular shock coil electrode 810 to right ventricular ring electrode 820, right ventricular shock coil electrode 810 to left ventricular distal electrode 822, right ventricular shock coil electrode 810 to left ventricular proximal electrode 824, right atrial shock coil electrode 812 to right atrial tip electrode 814, right atrial shock coil electrode 812 to right atrial ring electrode 816, right atrial shock coil electrode 812 to right ventricular tip electrode 818, right atrial shock coil electrode 812 to right ventricular ring electrode 820, right atrial shock coil electrode 812 to left ventricular distal electrode 822, right atrial shock coil electrode 812 to left ventricular proximal electrode 824, right atrial tip electrode 814 to right atrial ring electrode 816, right atrial tip electrode 814 to right ventricular tip electrode 818, right atrial tip electrode 814 to right ventricular ring electrode 820, right atrial tip electrode 814 to left ventricular distal electrode 822, right atrial tip electrode 814 to left ventricular proximal electrode 824, right atrial ring electrode 816 to right ventricular tip electrode 818, right atrial ring electrode 816 to right ventricular ring electrode 820, right atrial ring electrode 816 to left ventricular distal electrode 822, right atrial ring electrode 816 to left ventricular proximal electrode 824, right ventricular tip electrode 818 to left ventricular distal electrode 822, right ventricular tip electrode 818 to left ventricular proximal electrode 824, right ventricular ring electrode 820 to left ventricular distal electrode 822, right ventricular ring electrode 820 to left ventricular proximal electrode 824, and left ventricular distal electrode 822 to left ventricular proximal electrode 824. Other vectors may be formed, for example, by tying one or more other electrodes in common with one or the other of the electrodes of the pair. Moreover, as discussed above, the same electrodes may be used both to inject a test excitation current and to measure a responsive voltage (e.g., a two-point measurement). Alternatively, the test current introduction can share one electrode in common with the responsive voltage measurement, such as in a three-point measurement. In yet another alternative, the test current introduction can use different electrodes from the responsive voltage measurement, such as in a four-point measurement.

Additional or other Impedance Components

Although the above description has been described with particular emphasis on impedance-derived cardiac stroke and respiration signals, the above techniques can be used to select electrodes with respect to other impedance signals of interest, such as a near-DC signal representative of a subject's thoracic fluid status, including such excess of thoracic fluid such as due to pulmonary edema or pleural effusion, or deficiency of thoracic fluid such as due to orthostatic or other hypotension. In this document, the near-DC component of the thoracic impedance signal refers to the frequencies below which respiration and cardiac contractions significantly influence the thoracic impedance signal (e.g., at least an order of magnitude lower than the respiration component). In one example, the near-DC component of the thoracic impedance signal refers to signal frequencies below a cutoff frequency having a value of about 0.05 Hz, such as at signal frequencies between about $5 \times 10^{-7}$ Hz and 0.05 Hz, because the cardiac stroke and respiration components of the thoracic impedance signal lie at higher frequencies.

Figure 9:
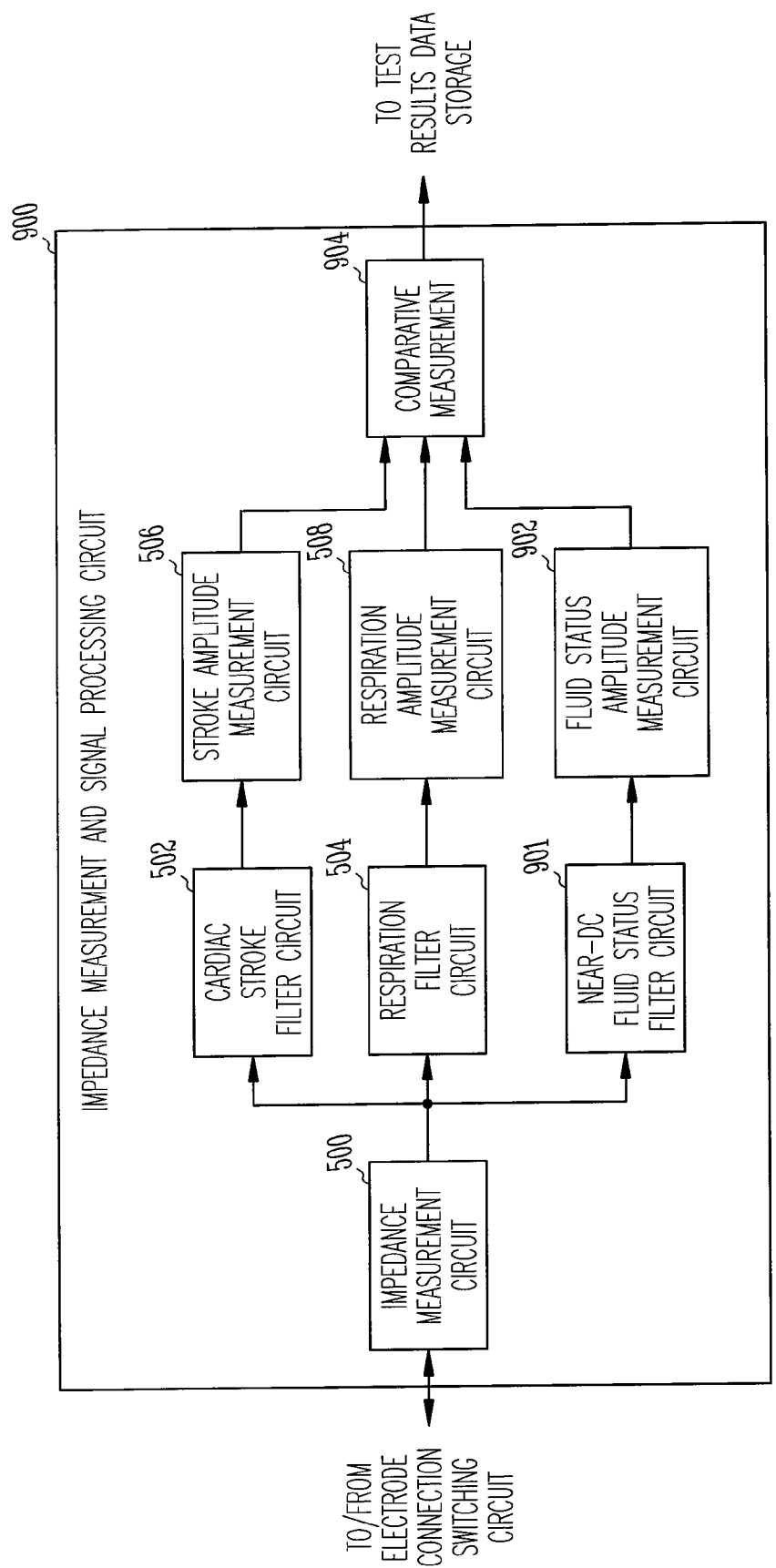
FIG. 9 illustrates an example of an impedance measurement and signal processing circuit that can be substituted for the impedance measurement and signal processing circuit of FIG. 5.

FIG. 9 illustrates an example of an impedance measurement and signal processing circuit 900 that can be substituted for the impedance measurement and signal processing circuit 319 of FIG. 5. In the example of FIG. 9, the impedance measurement and signal processing circuit 900 that includes a near-dc fluid status filter circuit 901 to measure thoracic fluid shifts, and a fluid status amplitude measurement circuit 902 to measure the amplitude of any such thoracic fluid shifts. In this example, the comparative measurement 904 is between at least one pair of the three input channels (e.g., cardiac stroke, respiration, and fluid status). Therefore, the impedance measurement and signal processing circuit 900 need only include two, but may include all three, of such channels.

In a further example, at least one integration, root-mean-square (RMS), or other signal aggregation circuit is included, such as between the cardiac stroke filter circuit 502 and the stroke amplitude measurement circuit 506 of FIG. 5 or FIG. 9 and between the respiration filter circuit 504 and the respiration amplitude measurement circuit 508 in FIG. 5 or FIG. 9. This permits the stroke or respiration amplitude measurement to be performed on the stroke or respiration signal after it has been processed to represent an aggregate signal value (e.g., over a period of time) rather than a single point amplitude measurement. This aggregation can be carried out over a single cardiac cycle (e.g., for an RMS stroke signal), a single respiration cycle (e.g., for an RMS respiration cycle), or over multiple such cardiac or respiration cycles, respectively. This aggregation represents an alternative technique for obtaining a central tendency of the stroke or respiration signal, instead of averaging, taking a median, or otherwise computing a central tendency of stroke or respiration amplitude measurements obtained at a single point in time.

Figure 10:
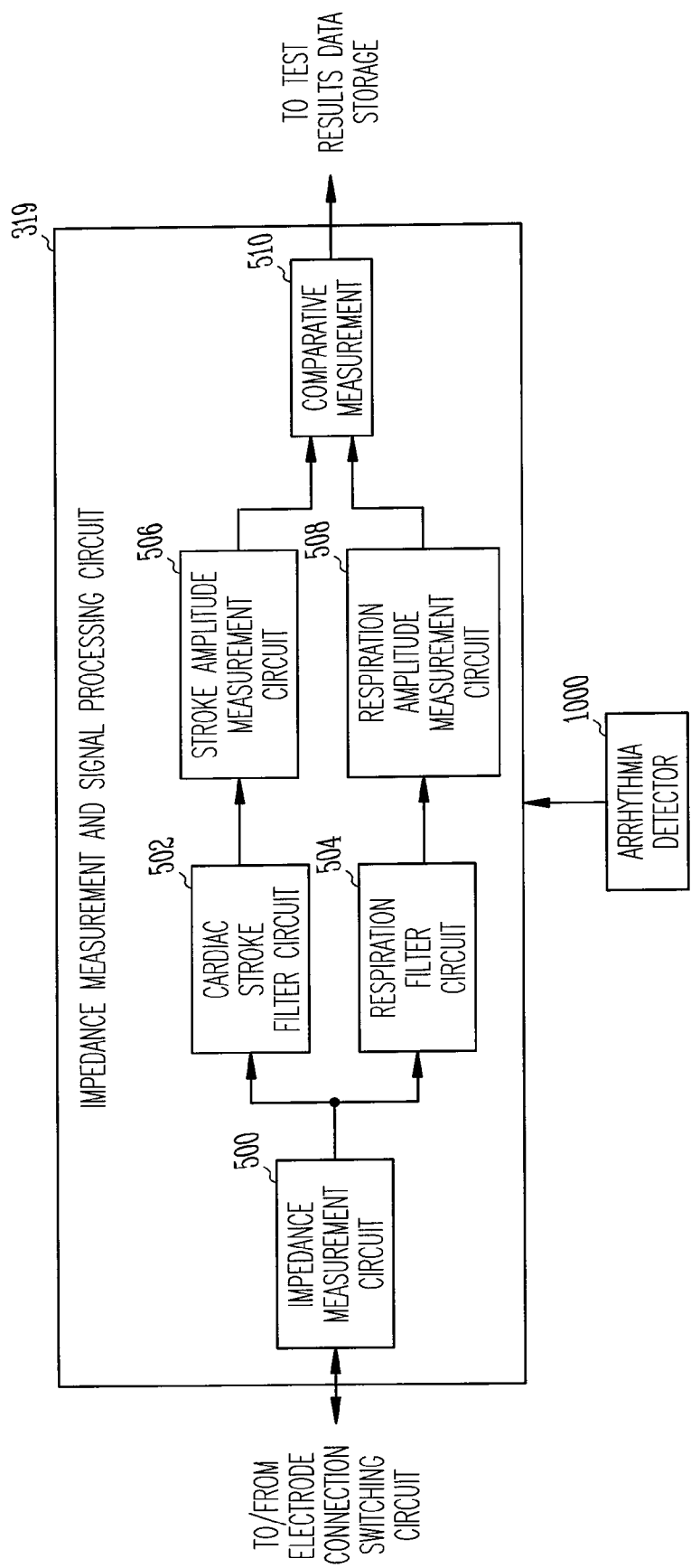
FIG. 10 is a block diagram of an example in which the IMD 302 includes an arrhythmia detector 1000 that is coupled to the impedance measurement and signal processing circuit 319 or the controller 318 to control operation such that stroke and respiration amplitudes are only obtained from heartbeats characteristic of normal sinus rhythm (NSR).

FIG. 10 is a block diagram of an example in which the IMD 302 includes an arrhythmia detector 1000 that is coupled to the impedance measurement and signal processing circuit 319 or the controller 318 to control operation such that stroke and respiration amplitudes are only obtained from heartbeats characteristic of normal sinus rhythm (NSR). In this example, arrhythmic heartbeats (e.g., premature ventricular contractions (PVCs), etc.) are excluded as a basis for calculating the ratios, differences, or other figures of merit discussed above. Excluding arrhythmic heartbeats may involve, among other things, inhibiting the impedance measurement circuit 500 during such beats or, more typically, discarding any stroke or respiration amplitudes, etc., measured during such PVCs or other beats deemed arrhythmic.

There are a number of ways in which NSR can be distinguished from arrhythmic heartbeats. For example, timer methods deem ventricular contractions that are detected before expected using the underlying NSR as being PVCs. In one example, a counter is incremented each time a PVC is detected, and any impedance measurements corresponding to such counter increments are invalidated. In another example morphology methods use the shape of the depolarization artifact to discriminate between NSR and arrhythmic beats. Examples of morphology-based techniques for such discrimination are described in Hsu U.S. Pat. No. 6,449,503, Hsu et al. U.S. Pat. No. 6,308,095, Hsu et al. U.S. Pat. No. 6,266,554, and Hsu et al. U.S. Pat. No. 6,438,410, each of which is incorporated by reference herein in its entirety, including its description of techniques for discriminating between NSR and arrhythmias. In one example, the impedance-based respiration or stroke measurements described above are invalidated for any beats deemed arrhythmic using such a morphological or other discrimination technique.

Conclusion

It is to be understood that the above description is intended to be illustrative, and not restrictive. For example, the above-described embodiments (and/or aspects thereof) may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in this document and in the following claims, the terms "first," "second," and "third," etc. are used merely as labels, and are not intended to impose numerical requirements on their objects.

What is claimed is:

1. A method comprising:
   measuring a first impedance signal between at least first and second electrodes, which define a first electrode configuration, in a subject's thorax;
   extracting a first cardiac stroke signal from the first impedance signal;
   extracting a first respiration signal from the first impedance signal;
   extracting a first cardiac amplitude measurement from the first cardiac stroke signal;
   extracting a first respiration amplitude measurement from the first respiration signal;
   computing a first comparative measurement between the first cardiac amplitude measurement and the first respiration amplitude measurement;
   measuring a second impedance signal between at least third and fourth electrodes, which define a second electrode configuration, in a subject's thorax, wherein at least one of the third and fourth electrodes is a different electrode from at least one of the first and second electrodes;
   extracting a second cardiac stroke signal from the second impedance signal;
   extracting a second respiration signal from the second impedance signal;
   extracting a second cardiac amplitude measurement from the second cardiac stroke signal;
   extracting a second respiration amplitude measurement from the second respiration signal;
   computing a second comparative measurement between the second cardiac amplitude measurement and the second respiration amplitude measurement; and
   using the first and second comparative measurements as a basis for selecting one of the first and second electrode configurations for subsequent extraction of at least one of the respiration and cardiac stroke signals.

2. The method of claim 1, in which:
   the computing the first comparative measurement includes computing a ratio between the first cardiac amplitude measurement and the first respiration amplitude measurement; and
   the computing the second comparative measurement includes computing a ratio between the second cardiac amplitude measurement and the second respiration amplitude measurement.

3. The method of claim 1, in which the using the first and second comparative measurements as a basis for selecting one of the first and second electrode configurations includes selecting the first electrode configuration if first comparative measurement exceeds the second comparative measurement.

4. The method of claim 3, in which the respiration signal is of interest and used in a diagnostic algorithm performed by an implantable medical device, and in which the first comparative measurement is one of: (1) a ratio of the first respiration signal to the first cardiac signal; and (2) a difference of the first respiration signal less the first cardiac signal; and in which the second comparative measurement is a comparable one of: (1) a ratio of the second respiration signal to the second cardiac signal; and (2) a difference of the second respiration signal less the second cardiac signal.

5. The method of claim 1, further comprising:
   comparing the first and second comparative measurements to a threshold value; and
   if the first and second comparative measurements are both less than the threshold value, then disabling the subsequent extraction of at least one of the respiration and cardiac stroke signals.

6. The method of claim 1, in which at least one of:
   the extracting the first cardiac amplitude measurement includes determining a central tendency of the first cardiac amplitude measurement over a plurality of cardiac cycles;
   the extracting the second cardiac amplitude measurement includes determining a central tendency of the second cardiac amplitude measurement over a plurality of cardiac cycles;
   the extracting the first respiration amplitude measurement includes determining a central tendency of the first respiration amplitude measurement over a plurality of respiration cycles; and the extracting the second respiration amplitude measurement includes determining a central tendency of the second respiration amplitude measurement over a plurality of respiration cycles.

7. The method of claim 1, including excluding the first cardiac amplitude measurement from consideration if a corresponding heartbeat is deemed arrhythmic.

8. A method comprising:
measuring a first impedance signal between at least first and second electrodes, which define a first electrode configuration, in a subject's thorax;
extracting a first cardiac stroke signal from the first impedance signal;
extracting a first respiration signal from the first impedance signal;
extracting a first cardiac amplitude measurement from the first respiration signal;
computing a first ratio by dividing the first respiration amplitude measurement by the first cardiac amplitude measurement;
measuring a second impedance signal between at least third and fourth electrodes, which define a second electrode configuration, in a subject's thorax, wherein at least one of the third and fourth electrodes is a different electrode from at least one of the first and second electrodes;
extracting a second cardiac stroke signal from the second impedance signal;
extracting a second respiration signal from the second impedance signal;
extracting a second cardiac amplitude measurement from the second cardiac stroke signal;
extracting a second respiration amplitude measurement from the second respiration signal;
computing a second ratio by dividing the second respiration amplitude measurement by the second cardiac amplitude measurement; and
selecting the first electrode configuration for subsequent extraction of the respiration signal if the first ratio exceeds the second ratio.

9. The method of claim 8, in which:
the first and third electrodes are configured as a common electrode that is located on a housing of a pectorally-implanted implantable medical device, and the second electrode is located in association with an atrium of the subject, and the fourth electrode is located in association with a ventricle of the subject.

10. The method of claim 8, further comprising:
comparing the first and second ratios to a threshold value; and
if the first and second ratios are both less than the threshold value, then disabling the subsequent extraction of at least one of the respiration signal over the second period of time.

11. A method comprising:
measuring a first impedance signal between at least first and second electrodes, which define a first electrode configuration, in a subject's thorax;
extracting a first cardiac stroke signal from the first impedance signal;
extracting a first respiration signal from the first impedance signal;
extracting a first cardiac amplitude measurement from the first stroke signal;
extracting a first respiration amplitude measurement from the first respiration signal;
computing a first ratio by dividing the first cardiac amplitude measurement by the first respiration amplitude measurement;
measuring a second impedance signal between at least third and fourth electrodes, which define a second electrode configuration, in a subject's thorax, wherein at least one of the third and fourth electrodes is a different electrode from at least one of the first and second electrodes;
extracting a second cardiac stroke signal from the second impedance signal;
extracting a second respiration signal from the second impedance signal;
extracting a second cardiac amplitude measurement from the second cardiac stroke signal;
extracting a second respiration amplitude measurement from the second respiration signal;
computing a second ratio by dividing the second cardiac amplitude measurement by the second respiration amplitude measurement; and
selecting the first electrode configuration for subsequent extraction of the cardiac signal if the first ratio exceeds the second ratio.

12. The method of claim 11, in which:
the first and third electrodes are configured as a common electrode that is located on a housing of a pectorally-implanted implantable medical device, and the second electrode is located in association with an atrium of the subject, and the fourth electrode is located in association with a ventricle of the subject.

13. The method of claim 11, further comprising:
comparing the first and second ratios to a threshold value; and
if the first and second ratios are both less than the threshold value, then disabling the subsequent extraction of at least one of the cardiac stroke signal.

14. A method comprising:
measuring impedance signals in a subject's thorax using different corresponding electrode configurations;
extracting, from each of the impedance signals, a cardiac stroke signal and a corresponding respiration signal obtained using the same electrode configuration as the corresponding cardiac stroke signal;
computing ratios between amplitudes of each cardiac stroke signal and the corresponding respiration signal; and
selecting a particular one of the electrode configurations for subsequently measuring an impedance signal to obtain at least one of an respiration signal and a cardiac stroke signal impedance-derived respiration, the selecting the particular one of the electrode configurations determined using values of the ratios relative to at least one of each other and a predefined threshold value.

15. The method of claim 14, in which the selecting the particular one of the electrode configurations includes choosing the particular one of the electrode configurations that corresponds to a largest respiration/stroke amplitude ratio among the computed ratios, and further comprising using the selected particular one of the electrode configurations for subsequently obtaining a respiration signal.

16. The method of claim 14, in which the selecting the particular one of the electrode configurations includes choosing the particular one of the electrode configurations that corresponds to a largest stroke/respiration amplitude ratio among the computed ratios, and further comprising using the selected particular one of the electrode configurations for subsequently obtaining a cardiac stroke signal.

17. A method comprising:
- measuring a first impedance signal between at least first and second electrodes, which define a first electrode configuration, in a subject's thorax;
- calculating a first figure of merit using the first impedance signal;
- measuring a second impedance signal between at least third and fourth electrodes, which define a second electrode configuration, in a subject's thorax, wherein at least one of the third and fourth electrodes is a different electrode from at least one of the first and second electrodes;
- calculating a second figure of merit using the second impedance signal; and
- using values of the first and second figures of merit as a basis for automatically selecting one of the first and second electrode configurations for subsequent diagnostic extraction of one of the first and second impedance signals;
- wherein the first and second figures of merit comprise at least one of: (1) an amplitude measurement of a respiration component of the first and second impedance signals, respectively; (2) an amplitude measurement of a cardiac stroke component of the first and second impedance signals, respectively; or (3) an amplitude measurement of a near-DC fluid status component of the first and second impedance signals, respectively.

18. The method of claim 17, further comprising:
- placing an implantable medical device in a test mode for performing the acts of measuring the first and second impedance signals, calculating the first and second figures of merit, and automatically selecting one of the first and second electrode configurations;
- exiting the test mode and placing an implantable medical device in a diagnostic mode; and
- extracting diagnostic impedance data, in the diagnostic mode, using the selected one of the first and second electrode configurations.

19. The method of claim 18, further comprising repeatedly placing the implantable medical device in a test mode for performing the acts of measuring the first and second impedance signals, calculating the first and second figures of merit, and automatically selecting one of the first and second electrode configurations.

20. The method of claim 18, further comprising triggering the test mode upon detecting at least one of a change in heart rate and a change in posture.

21. The method of claim 17, in which the first and second figures of merit comprise an amplitude measurement of a respiration component of the first and second impedance signals, respectively.

22. The method of claim 17, in which the first and second figures of merit comprise an amplitude measurement of a cardiac stroke component of the first and second impedance signals, respectively.

23. The method of claim 17, in which the first and second figures of merit comprise an amplitude measurement of a near-DC fluid status component of the first and second impedance signals, respectively.

24. The method of claim 17, in which the first and second figures of merit comprise a noise measurement of a respiration component of the first and second impedance signals, respectively.

25. The method of claim 24, in which the noise measurement of the respiration component of the respective first and second impedance signals comprises a cardiac stroke component of the respective first and second impedance signals.

26. The method of claim 17, in which the first and second figures of merit comprise a noise measurement of a cardiac stroke component of the first and second impedance signals, respectively.

27. The method of claim 26, in which the noise measurement of the cardiac stroke component of the respective first and second impedance signals comprises a respiration component of the respective first and second impedance signals.

* * * * *

UNITED STATES PATENT AND TRADEMARK OFFICE
CERTIFICATE OF CORRECTION

PATENT NO. : 7,630,763 B2  Page 1 of 1
APPLICATION NO. : 11/110418
DATED : December 8, 2009
INVENTOR(S) : Jonathan Kwok et al.

It is certified that error appears in the above-identified patent and that said Letters Patent is hereby corrected as shown below:

In column 13, lines 16-17, in Claim 8, delete "extracting a first cardiac amplitude measurement from the first respiration signal;" and insert -- extracting a first cardiac amplitude measurement from the first cardiac stroke signal; extracting a first respiration amplitude measurement from the first respiration signal; --, therefor.

In column 13, line 65, in Claim 11, delete "first stroke" and insert -- first cardiac stroke --, therefor.

Signed and Sealed this

Twenty-third Day of March, 2010

David J. Kappos
*Director of the United States Patent and Trademark Office*

UNITED STATES PATENT AND TRADEMARK OFFICE
CERTIFICATE OF CORRECTION

PATENT NO. : 7,630,763 B2 Page 1 of 1
APPLICATION NO. : 11/110418
DATED : December 8, 2009
INVENTOR(S) : Kwok et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1267 days.

Signed and Sealed this

Twenty-first Day of December, 2010

David J. Kappos
*Director of the United States Patent and Trademark Office*